US011149240B2

United States Patent
Kang et al.

(10) Patent No.: US 11,149,240 B2
(45) Date of Patent: Oct. 19, 2021

(54) ROTARY DEVICE FOR BIO-PRINTING AND METHOD FOR USING THE SAME

(71) Applicant: REVOTEK CO., LTD, Sichuan (CN)

(72) Inventors: Yujian James Kang, Sichuan (CN); Huixing Zhou, Sichuan (CN)

(73) Assignee: REVOTEK CO., LTD, Sichuan (CN)

( * ) Notice: Subject to any disclaimer, the term of this patent is extended or adjusted under 35 U.S.C. 154(b) by 842 days.

(21) Appl. No.: 15/562,560

(22) PCT Filed: Mar. 31, 2015

(86) PCT No.: PCT/CN2015/075469
§ 371 (c)(1),
(2) Date: Sep. 28, 2017

(87) PCT Pub. No.: WO2016/154882
PCT Pub. Date: Oct. 6, 2016

(65) Prior Publication Data
US 2018/0112167 A1    Apr. 26, 2018

(51) Int. Cl.
*C12M 3/00* (2006.01)
*A61F 2/04* (2013.01)
(Continued)

(52) U.S. Cl.
CPC ............... *C12M 21/08* (2013.01); *A61F 2/04* (2013.01); *A61F 2/06* (2013.01); *A61L 27/36* (2013.01);
(Continued)

(58) Field of Classification Search
CPC ....... C12M 23/06; C12M 21/08; C12M 33/00
See application file for complete search history.

(56) References Cited

U.S. PATENT DOCUMENTS

| 2002/0049489 | A1  | 4/2002  | Herweck et al. |
| 2010/0330144 | A1  | 12/2010 | Liu et al. |
| 2014/0014751 | A1* | 1/2014  | Sampaio ............... A47J 43/255 241/93 |

FOREIGN PATENT DOCUMENTS

| CN | 101294131 A | 10/2008 |
| CN | 103462725 A | 12/2013 |

(Continued)

OTHER PUBLICATIONS

International Search Report dated Jan. 5, 2016 issued in PCT/CN2015/075469.

(Continued)

*Primary Examiner* — Teresa E Knight
(74) *Attorney, Agent, or Firm* — Scully Scott Murphy & Presser

(57) ABSTRACT

The present invention relates to a rotary rod for 3D bio-printing, in which the rotary rod is arranged horizontally and is driven to rotate, the rotary rod has a hollow structure and provided with at least one hole in a surface thereof, such that during a 3D bio-printing process, a nutrition solution passes through the hollow structure and a portion of the nutrition solution exudes via at least one hole. The present invention further provides a 3D bio-printing platform for supplying nutrition, comprising the rotary rod and a nutrition supply system, and a method of printing a tubular tissue using the bio-printing platform. The present invention, which reduces the possibility of resulting in tissue collapse from the effect of gravity, provides a new method of 3D bio-printing a tubular tissue and supplying nutrition in a printing process, with a wide application prospect.

18 Claims, 1 Drawing Sheet

(51) Int. Cl.
- *B33Y 10/00* (2015.01)
- *B33Y 30/00* (2015.01)
- *B29C 64/112* (2017.01)
- *B29C 64/209* (2017.01)
- *B29C 64/321* (2017.01)
- *A61F 2/06* (2013.01)
- *A61L 27/36* (2006.01)
- *C12M 1/12* (2006.01)
- *C12M 1/00* (2006.01)
- *C12M 1/26* (2006.01)
- *C12N 5/00* (2006.01)
- *B29C 64/218* (2017.01)
- *B33Y 70/00* (2020.01)

(52) U.S. Cl.
CPC .......... *B29C 64/112* (2017.08); *B29C 64/209* (2017.08); *B29C 64/321* (2017.08); *B33Y 10/00* (2014.12); *B33Y 30/00* (2014.12); *C12M 3/00* (2013.01); *C12M 23/06* (2013.01); *C12M 29/00* (2013.01); *C12M 33/00* (2013.01); *C12N 5/0062* (2013.01); *A61F 2240/001* (2013.01); *A61L 2400/18* (2013.01); *B29C 64/218* (2017.08); *B33Y 70/00* (2014.12)

(56) References Cited

FOREIGN PATENT DOCUMENTS

| | | |
|---|---|---|
| CN | 104146793 A | 11/2014 |
| CN | 104146794 A | 11/2014 |
| JP | 2006-141290 A | 6/2006 |
| JP | 2008-29866 A | 2/2008 |
| WO | 98/25546 A1 | 6/1998 |
| WO | 03/079985 A2 | 10/2003 |
| WO | 2007/136227 A1 | 11/2007 |

OTHER PUBLICATIONS

Japanese Notice of Reasons for Rejection dated Dec. 4, 2018 received in Japanese Patent Application No. 2018-502296, together with an English-language translation.

Extended Supplementary European Search Report dated Oct. 31, 2018 in European Patent Application No. 15 88 6868.7.

* cited by examiner

ROTARY DEVICE FOR BIO-PRINTING AND METHOD FOR USING THE SAME

FIELD OF THE INVENTION

The present invention relates to a bio-engineering manufacturing technique in the field of tissue engineering, and more particularly, relates to a rotary rod for 3D bio-printing, a 3D bio-printing platform for supplying nutrition, and a method of printing a tubular tissue using the platform.

BACKGROUND OF THE INVENTION

The blood vessel, which zigzags in our organism, functions as transporting necessary nutritional substances and excreting toxic wastes, so as to guarantee normal operation of our organs. To develop a new artificial blood vessel has always been a long-standing problem. With the increase of aging population, the gradually worsened circumstances such as abdominal aortic aneurysm and vascular embolization, and the increasing demands for artificial vessels, various types of artificial blood vessels have also successively come into existence. With the development of modern bio-engineering and materials science, many new artificial materials and techniques have attained wide application in the field of vascular surgery. At present, the materials commonly used for manufacturing artificial blood vessels are mostly polymer or synthetic materials such as Nylon, Orlon, Ivalon, Dacron, Teflon, ePTFE, Silk, but these types of materials are all present with circumstances such as poor biocompatibility, short service life, a vascular diameter that is hard to go below 6 mm and vulnerability to vascular embolization.

A research group for 3D printing of tissue (including blood vessel) from Wyss Institute of Harvard University, printed special material containing extracellular matrix and living cells in a filamentous form according to a predetermined position, shape and size, then melted such special material by cooling, such that in the printed tissue, a lumen structure may be formed at a position where the special material is located, then endothelial cells are injected at a position of the lumen, and afterwards the cells regrow into a vascular structure at a position of the lumen.

Cyfuse Biomedical K.K., Japan, utilizes Kenzan Technology, or Micro Needle Array Technology, to print cells to form a tubular tissue, which inserts the cells on micro needle array according to a predetermined shape to form a tubular tissue structure, in such a manner as to solve the problem of collapse of a printed tissue resulting from a gravitational effect in a printing process, but present with a restriction in a printing length. The nutritional supply of cells in its printed tissue is accomplished by immersing the micro needle array in a nutrition solution.

Among existing 3D printing technologies, when a tubular tissue is being printed, some cannot directly use bioink (3D bio-printing materials) to scaffold-freely create a predetermined lumen tissue structure by printing as required, and some are subjected to restriction in a printing length. In addition, it is also necessary to consider the problem of nutrition supply for cells in a printing process so that the cells can maintain a favorable activity after printing.

SUMMARY OF THE INVENTION

In order to overcome the aforementioned defects of current 3D bio-printing technologies when printing a tubular tissue, the present invention relates to a rotary rod for 3D bio-printing, in which the rotary rod is arranged horizontally and is driven to rotate, the rotary rod has a hollow structure and provided with at least one hole in a surface thereof, such that during a 3D bio-printing process, a nutrition solution passes through the hollow structure and a portion of the nutrition solution exudes via the at least one hole.

In one embodiment, the rotary rod is rotatably driven by a motor having a controllable rotation speed to rotate, and at least one end of the rotary rod can be detachable.

In one embodiment, the surface of the rotary rod is coated with at least one layer of liquid-permeable biocompatible substance.

In one embodiment, the biocompatible substance comprises a biocompatible hydrogel or a porous polymeric film.

In one embodiment, the biocompatible hydrogel is removable or separable by a biological, physical or chemical method comprising temperature control, pH adjustment, enzymolysis and chemical reaction.

In one embodiment, the biocompatible substance is formed of one or more of the following materials by means of chemical modification, copolymerization, physical blending or surface modification: a gelatin material and a complex thereof, saturated fatty acid, poly(N, N-diethylacrylamide), hydroxypropyl methyl cellulose, polylactic acid, polycaprolactone, poly(lactide-co-glycolide), poly(N-isopropyl acrylamide), poly(2-(N,N-dimethylamino)ethyl methacrylate), poly(ethylene oxide), and derivatives thereof.

In one embodiment, the rotary rod is of a material presenting mechanical strength, and having a shape, structure, length and aperture size thereof individually based on a tubular tissue required to be printed.

The present invention further provides a 3D bio-printing platform for supplying nutrition, which comprises the rotary rod and a nutrition supply system, in which during a 3D bio-printing process, the nutrition supply system delivers a nutrition solution to the rotary rod, such that the nutrition solution passes through the hollow structure of the rotary rod and a portion of the nutrition solution exudes via at least one hole in a surface of the rotary rod.

In one embodiment, the rotary rod has a first end and a second end, the nutrition supply system comprises a nutrition solution container; a nutrition solution delivery tube, with one end extending into the nutrition container and the other end leading to the first end of the rotary rod; a nutrition solution return tube, with one end leading to the second end of the rotary rod and the other end extending into the nutrition container, and a pump located in a line of the nutrition delivery tube, such that during a 3D bio-printing process, the nutrition solution is sucked into the nutrition solution tube by the pump and enters the hollow structure of the rotary rod, so that a portion of the nutrition solution in the hollow structure exudes via at least one hole in the surface of the rotary rod, and the other portion of the nutrition solution is recycled into the nutrition solution container through the hollow structure and the nutrition solution return tube.

In one embodiment, the flow velocity of the nutrition solution is controllable.

In one embodiment, the line of the nutrition solution return tube is provided with a filtering means.

In one embodiment, the temperature of the 3D bio-printing platform is controllable.

The present invention further provides a method of printing a tubular tissue using the 3D bio-printing platform, which comprises the following steps: driving a rotary rod to rotate; and delivering a nutrition solution to the rotary rod by a nutrition supply system during a 3D bio-printing process, such that the nutrition solution passes through a hollow structure of the rotary rod and a portion of the nutrition solution exudes via at least one hole in a surface of the rotary rod.

In one embodiment, the method further comprises a step of utilizing a computer to assist in designing a rotary rod by modeling according to body parameters or direct 3D modeling, and making a rotary rod.

In one embodiment, the step of utilizing a computer to assist in designing a rotary rod comprises utilizing a 3D modeling software and/or simulation technique to set parameters including mechanical strength, diameter, length, tube wall thickness, flexure and surface roughness of the rotary rod, shape, porosity, pore distribution, and aperture size of a hole in the surface of the rotary rod.

In one embodiment, the method further comprises a step of coating at least one layer of liquid-permeable biocompatible substance to a surface of the rotary rod.

In one embodiment, the method further comprises a step of printing bioink, while the nutrition solution exudes from the biocompatible substance via at least one hole in the surface of the rotary rod.

In one embodiment, the flow velocity of the nutrition solution is regulated by a pump.

In one embodiment, the nutrition solution is sprayed to the surface of the rotary rod from outside.

In one embodiment, the method further comprises the steps of removing or separating the biocompatible substance from the surface of the rotary rod, removing the tubular tissue from the rotary rod and performing cultivation after printing and moulding the tubular tissue.

In one embodiment, the method further comprises the steps of removing the rotary rod with the tubular tissue and culturing after dimensional printing the tubular tissue, and then removing the tubular tissue from the rotary rod after culturing.

Compared with current methods for 3D bio-printing a tubular tissue, the present invention has the following advantages:

1) The rotary rod of the present invention is hollow and porous, it solves the problem of nutrition supply in a printing process, so that the cells may maintain the bioactivity as much as possible, and also facilitate the biostimulation such as shearing force of the printed tubular tissue, thereby promotes cell growth and development;

2) Customises the printing platform for tubular tissue—the rotary rod, which is horizontally arranged, to reduce the effect of gravity;

3) The rotary rod is conveniently disassemble, after dimensional printing, by removing or separating a biocompatible substance from the surface of the rotary rod, a tubular tissue may be removed from the rotary rod and cultured (for example placed in an incubator), or the rotary rod with the tubular tissue is removed and cultured (for example placed in an incubator), and then the tubular tissue may be removed from the rotary rod after cultured.

BRIEF DESCRIPTION OF THE ACCOMPANYING DRAWINGS

DETAILED DESCRIPTION OF THE PREFERRED EMBODIMENTS

In order to further explain the object, technical solution and advantages of the present invention, the present invention will be further described in detail in combination with the drawings as follows. It should be noted that the embodiments that are described here are only used for explaining the present invention, rather than limiting the scope of the present invention.

It is necessary to explain that, the "3D bio-printing" mentioned in the present invention may also be referred to in the art as "additive manufacturing" or "three-dimensional printing".

Figure 1:
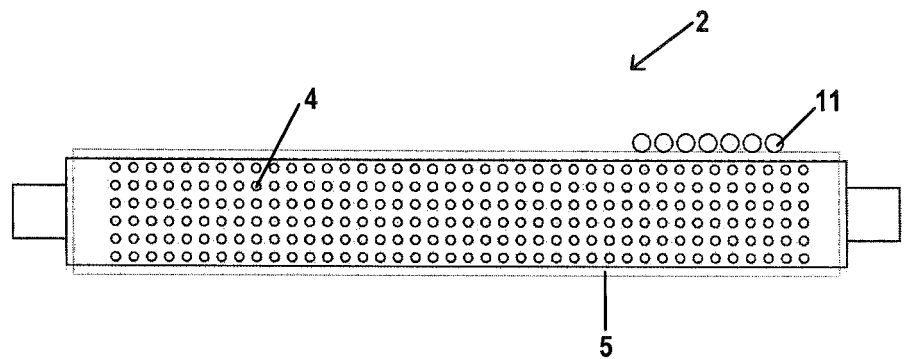
FIG. 1 illustrates a rotary rod for 3D bioprinting according to an embodiment of the present invention.

With reference to FIG. 1, it illustrates a rotary rod 2 for 3D bioprinting according to an embodiment of the present invention. The rotary rod 2 is arranged horizontally and is driven to rotate. The rotary rod 2 has a hollow structure and provided with at least one hole 4 in a surface thereof, such that during a 3D bio-printing process, a nutrition solution (mainly used for supplying nutrition in a tubular tissue printing process, so as to improve the bioactivity of cells) passes through the hollow structure and a portion of the nutrition solution exudes via the at least one hole 4. The rotary rod 2 may be rotatably driven by the motor to rotate, and may also be rotated by other driving sources or in other driving manners to rotate. Under the circumstance of using a motor, at least one end of the rotary rod 2 may be directly connected to the motor by a bushing, indirectly connected to the motor by a shaft and a transmission mechanism, connected to the motor by magnetic drive, or connected to the motor in any other manners capable of driving rotation of the rotary rod 2. The motor is preferably a rotation speed controllable motor, such as a servo motor or a stepper motor capable of precisely regulating a speed, and certainly any other type of motor known in the art may also be used as a substitution. In the case where only one end of the rotary rod 2 is connected to the motor, the other end of the rotary rod 2 is suspended or supported by a support frame. At least one end of the rotary rod 2 is detachable. The material of the rotary rod 2 is required to have certain mechanical strength, for example, may be made of such materials as metal (such as stainless steel, aluminum alloy, titanium alloy), polymeric materials, inorganic materials, and its shape, structure, length and pore size may be individually based on the parameters (for example the structure and the size) of the tubular tissue required to be printed. The parameters of at least one hole 4 of the rotary rod 2 such as the size, shape, density and distribution are mainly determined based on the diameter of a tubular tissue required to be printed and the simulation of intra-body mechanics. At least one hole 4 in the 3D bioprinting process is used for a nutrition solution to exude from inside the rotary rod 2, and at the same time, at least one hole 4 also facilitates the biostimulation such as shearing force of a printed vessel, thereby promoting cell growth and development.

The surface of the rotary rod 2 may be coated with at least one layer of liquid-permeable biocompatible substance 5. The nutrition solution may be permeated out of the surface coating through the at least one hole 4 in the surface of the rotary rod 2, to form a slightly moisturized nutrition supply platform having a support capability, and the surface coating may also be used for exchanging nutrient substances. The surface coating which presents biological safety, possesses certain mechanical support strength, and is not mutually soluble and easily separated from a printing material. In one embodiment, the biocompatible substance of the surface coating is a biocompatible hydrogel removable or separable by a biological, physical or chemical method comprising temperature control, pH adjustment, enzymolysis and chemical reaction, and the biocompatible hydrogel may preferably be degradable by temperature control. In another embodiment, the biocompatible substance of the surface coating is a porous polymeric film, such as a porous film made of PLA, PCL, PLGA. The biocompatible substance may be formed of one or more of the following materials by means of chemical modification, copolymerization, physical blending or surface modification: a gelatin material and a complex thereof, saturated fatty acid, poly(N, N-diethyl-acrylamide), hydroxypropyl methyl cellulose, polylactic acid, polycaprolactone, poly(lactide-co-glycolide), poly(N-isopropyl acrylamide), poly(2-(N,N-dimethylamino)ethyl methacrylate), poly(ethylene oxide), and derivatives thereof.

Figure 2:
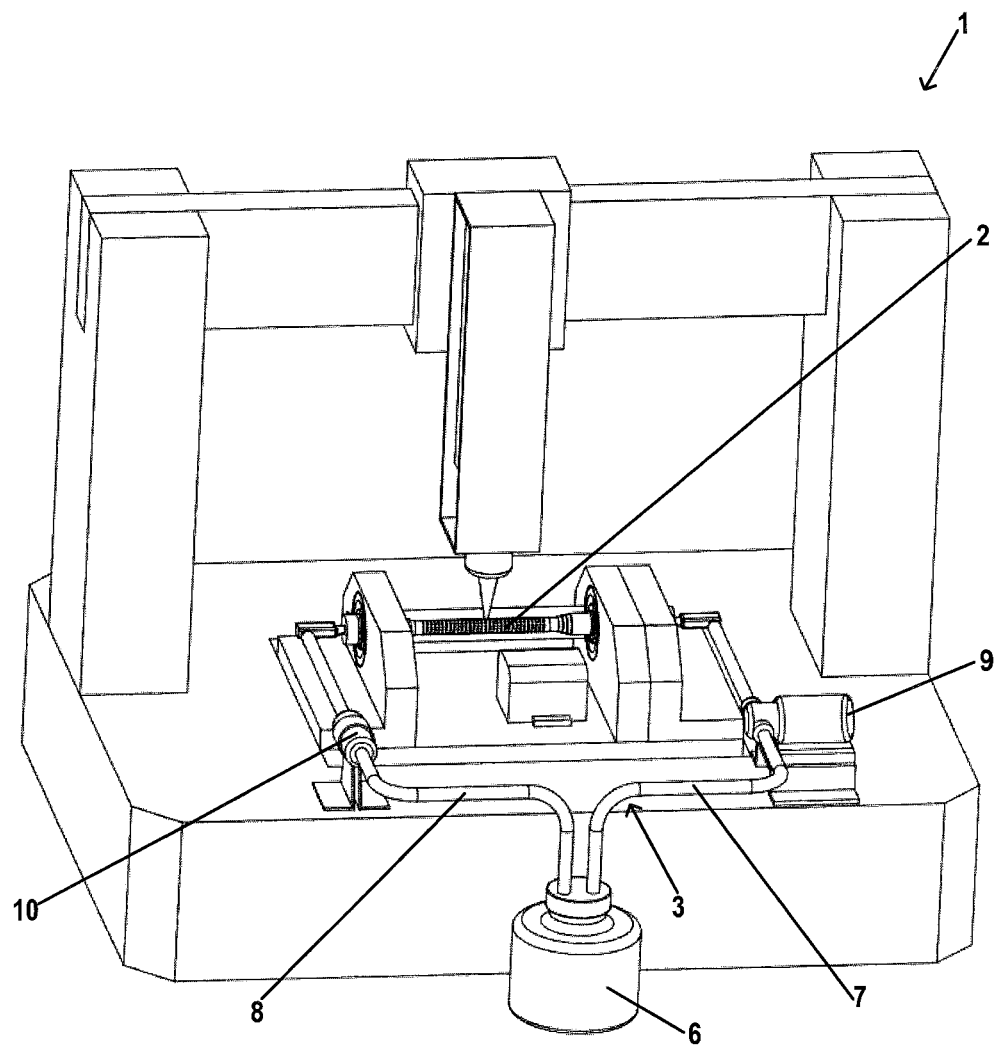
FIG. 2 illustrates an overall structure of a 3D bio-printing platform for supplying nutrition according to an embodiment of the present invention.

Now with reference to FIG. 2, it illustrates an overall structure of a 3D bio-printing platform for supplying nutrition according to an embodiment of the present invention. The bioprinting platform which is generally presented by reference sign 1, mainly consists of a rotary rod 2 serving as a printing support rod and a nutrition supply system 3 for supplying nutrition. As illustrated in FIG. 2, the nutrition supply system 3 comprises a nutrition solution container 6; a nutrition solution delivery tube 7, with one end extending into the nutrition container 6 and the other end leading to an end of the rotary rod 2; a nutrition solution return tube 8, with one end leading to the other end of the rotary rod 2 and the other end extending into the nutrition container 6, and a pump 9 located in a line of the nutrition delivery tube 7, such that during a 3D bio-printing process, the nutrition solution is sucked into the nutrition solution delivery tube 7 by the pump 9 and enters the hollow structure of the rotary rod 2, so that a portion of the nutrition solution in the hollow structure exudes via at least one hole 4 in a surface of the rotary rod 2, and the other portion of the nutrition solution is recycled into the nutrition solution container 6 through the hollow structure and via the nutrition solution return tube 8. The nutrition solution may be an ordinary nutrition solution, and may also have special additive ingredients. The flow velocity of the nutrition solution is controllable. In one embodiment, the flow velocity of the nutrition solution may be regulated by a pump 9 located in the line of the nutrition solution delivery tube 7, and other flow velocity control means may also be utilized as long as it can be ensured that the nutrition solution exudes from the surface of the rotary rod 2. In an alternative embodiment, the line of the nutrition solution return tube 8 is provided with a filtering means 10 to perform a filtering treatment of the nutrition solution returned into the nutrition container 6. In addition, the rotary printing platform is a printing platform for supplying nutrition to different tissues and individual designs, and the nutrition supply manner is a manner of intra-platform permeation, or external spray or both of the two at the same time. In one embodiment of external spray, the nutrition solution is sprayed from outside towards the surface of the rotary rod 2, so as to supply nutrition for cell printing. The temperature of the rotary printing platform is controllable, for example the regulation of the temperature may be effectuated by control of a temperature of the nutrition solution and by regulation of the ambient temperature.

The method of printing a tubular tissue using the 3D bio-printing platform may comprise: driving a rotary rod to rotate; and delivering a nutrition solution to the rotary rod by a nutrition supply system during a 3D bio-printing process, such that the nutrition solution passes through a hollow structure of the rotary rod and a portion of the nutrition solution exudes via at least one hole in a surface of the rotary rod.

The method may further comprise a step of utilizing a computer to assist in designing a rotary rod by modeling according to body parameters or direct 3D modeling, before making a rotary rod. Modeling according to body parameters refers to such a manner that data parameters are obtained by body scanning (such as MRI or CT) or other existing technical means, and then converted into three-dimensional model by assistance of a computer. Direct 3D modeling refers to direct 3D modeling by parameters. The step of utilizing a computer to assist in designing a rotary rod comprises utilizing a 3D modeling software and/or simulation technique to set parameters including mechanical strength, diameter, length, tube wall thickness, flexure and surface roughness of the rotary rod, shape, porosity, pore distribution, and aperture size of a hole in the surface of the rotary rod. The production of the rotary rod may include the production of a rotary rod by a conventional method and a rotary rod printed by a 3D printer.

The method may further comprise the steps of coating at least one layer of liquid-permeable biocompatible substance to a surface of the rotary rod; printing bioink (see FIG. 1), so that the nutrition solution exudes from the biocompatible substance via at least one hole in the surface of the rotary rod; and after a tubular tissue is printed and moulded, removing or separating a biocompatible substance on the surface of the rotary rod and then removing a tubular tissue from the rotary rod and culturing the same (for example placed in an incubator), or after a tubular tissue is printed, removing the rotary rod with the tubular tissue and culturing the same (for example placed in an incubator). During the process of performing cultivation, the entire rotary rod may offer mechanics-related stimulation to a printed tissue through a hole channel, or offer mechanical, biological and chemical stimuli externally.

The present invention, which reduces the possibility of resulting in tissue collapse from the effect of gravity, provides a new method of 3D bio-printing a tubular tissue and supplying nutrition in a printing process, with a wide application prospect.

The present invention is not limited to the aforementioned embodiments. If any change and modification to the present invention does not depart from the spirit and scope of the present invention, in the case that such change and modification fall into the scope of the claims of the present invention as well as equivalent arts, the present invention also intends to contain such change and modification.

The invention claimed is:

1. A 3D bio-printing platform for supplying nutrition, comprising:
   a rotary rod comprising:
   at least one end configured to be connected to a motor, such that the rotary rod is rotatable by the motor and is arranged horizontally:
   a hollow structure configured to permit a nutrition solution to pass through the
   hollow structure during a 3D bio-printing process using a bio-printing material: and
   at least one hole formed through the hollow structure for exuding a portion of the nutrition solution out of the hollow structure as the nutrition solution passes through the hollow structure, wherein the bio-printing material comprises living cells and the nutrition solution supplies nutrition to the bio-printing material to improve the bioactivity of the living cells; and a nutrition supply system, wherein, the nutrition supply system is configured to deliver the nutrition solution to the rotary rod, such that the nutrition solution passes through the hollow structure of the rotary rod and the portion of the nutrition solution exudes out of the hollow structure via the at least one hole, during the 3D bio-printing process.

2. The 3D bio-printing platform of claim 1, wherein the rotary rod has a first end and a second end, the nutrition supply system comprises:

a nutrition solution container for accommodating the nutrition solution; a nutrition solution delivery tube, one end of which extends into the nutrition container and the other end leads to the first end of the rotary rod;

a nutrition solution return tube, one end of which leads to the second end of the rotary rod and the other end extends into the nutrition container; and a pump located in a line of the nutrition delivery tube, wherein the pump is configured to suck the nutrition solution into the nutrition solution tube to permit the nutrition solution to enter the hollow structure of the rotary rod, so that the portion of the nutrition solution in the hollow structure exudes out of the hollow structure via the at least one hole, and the rest of the nutrition solution is recycled into the nutrition solution container through the hollow structure and the nutrition solution return tube, during the 3D bioprinting process.

3. The 3D bio-printing platform of claim 2, wherein the pump is configured to control a flow velocity of the nutrition solution.

4. The 3D bio-printing platform of claim 2, wherein the line of the nutrition solution return tube is provided with a filtering means.

5. The 3D bio-printing platform of claim 1, wherein the temperature of the 3D bio-printing platform is controllable.

6. The 3D bio-printing platform of claim 1, wherein a surface of the rotary rod is coated with at least one layer of liquid-permeable biocompatible substance.

7. The 3D bio-printing platform of claim 6, wherein said biocompatible substance comprises a biocompatible hydrogel or a porous polymeric film.

8. The 3D bio-printing platform of claim 6, wherein said biocompatible substance is formed of one or more of the following materials by means of chemical modification, copolymerization, physical blending or surface modification: a gelatin material and a complex thereof, saturated fatty acid, poly(N, N-diethylacrylamide), hydroxypropyl methyl cellulose, polylactic acid, polycaprolactone, poly(lactide-co-glycolide), poly(N-isopropyl acrylamide), poly(2-(N,N-dimethylamino)ethyl methacrylate), poly(ethylene oxide), and derivatives thereof.

9. The 3D bio-printing platform of claim 1, wherein the rotary rod is of a material presenting mechanical strength, and having a shape, structure, length and aperture size thereof which is individually based on a tubular tissue required to be printed.

10. A method of printing a tubular tissue using the 3D bio-printing platform of claim 1, comprising the following steps:

driving a rotary rod to rotate; and delivering a nutrition solution to the rotary rod by a nutrition supply system during a 3D bio-printing process, such that the nutrition solution passes through a hollow structure of the rotary rod and a portion of the nutrition solution exudes via at least one hole in a surface of the rotary rod.

11. The method of claim 10, further comprising a step of utilizing a computer to assist in designing a rotary rod by modeling according to body parameters or direct 3D modeling, and making a rotary rod.

12. The method of claim 11, wherein the step of utilizing a computer to assist in designing a rotary rod comprises utilizing a 3D modeling software and/or simulation technique to set parameters including mechanical strength, diameter, length, tube wall thickness, flexure and surface roughness of the rotary rod, shape, porosity, pore distribution and aperture size of a hole in a surface of the rotary rod.

13. The method of claim 11, further comprising a step of coating at least one layer of liquid-permeable biocompatible substance to a surface of the rotary rod.

14. The method of claim 13, further comprising a step of printing bioink while the nutrition solution exudes from the biocompatible substance via at least one hole in the surface of the rotary rod.

15. The method of claim 14, wherein the flow velocity of the nutrition solution is regulated by a pump.

16. The method of claim 14, further comprising a step of removing or separating the biocompatible substance from the surface of the rotary rod, removing a tubular tissue from the rotary rod and culturing after dimensional printing the tubular tissue.

17. The method of claim 14, further comprising a step of removing the rotary rod with a tubular tissue and culturing after dimensional printing the tubular tissue, and then removing the tubular tissue from the rotary rod after culturing.

18. The method of claim 10, further comprising a step of spraying the nutrition solution to the surface of the rotary rod from outside.

* * * * *